(12) United States Patent
Schwarz et al.

(10) Patent No.: US 9,187,412 B2
(45) Date of Patent: Nov. 17, 2015

(54) PROCESS FOR PREPARING 3-CYANO-3,5,5-TRIMETHYLCYCLOHEXANONE

(75) Inventors: Markus Schwarz, Haltern am See (DE); Andreas Merkel, Recklinghausen (DE); Joerg-Joachim Nitz, Essen (DE); Gerda Grund, Coesfeld (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/124,449

(22) PCT Filed: Jun. 5, 2012

(86) PCT No.: PCT/EP2012/060577
§ 371 (c)(1),
(2), (4) Date: Dec. 6, 2013

(87) PCT Pub. No.: WO2012/171830
PCT Pub. Date: Dec. 20, 2012

(65) Prior Publication Data
US 2014/0114085 A1  Apr. 24, 2014

(30) Foreign Application Priority Data
Jun. 17, 2011  (DE) .................. 10 2011 077 681

(51) Int. Cl.
*C07C 253/10* (2006.01)
*C07C 253/30* (2006.01)

(52) U.S. Cl.
CPC ............ *C07C 253/30* (2013.01); *C07C 253/10* (2013.01)

(58) Field of Classification Search
CPC .... C07C 253/10; C07C 253/30; C07C 255/46
See application file for complete search history.

(56) References Cited

U.S. PATENT DOCUMENTS

| | | | |
|---|---|---|---|
| 5,183,915 A | 2/1993 | Forguy et al. | |
| 6,822,110 B2 * | 11/2004 | Kunsmann-Keitel et al. | 558/315 |
| 7,652,165 B2 * | 1/2010 | Oftring et al. | 558/341 |
| 8,536,370 B2 | 9/2013 | Grund et al. | |
| 2004/0092761 A1 | 5/2004 | Kunsmann-Keitel et al. | |
| 2006/0058544 A1 | 3/2006 | Oftring et al. | |
| 2009/0048466 A1 | 2/2009 | Lettmann et al. | |
| 2010/0041921 A1 | 2/2010 | Lettmann et al. | |
| 2013/0253226 A1 | 9/2013 | Galle et al. | |
| 2013/0261341 A1 | 10/2013 | Lettmann et al. | |
| 2013/0261343 A1 | 10/2013 | Orschel et al. | |

FOREIGN PATENT DOCUMENTS

| | | |
|---|---|---|
| CN | 101851178 | 10/2010 |
| EP | 1 418 172 A2 | 5/2004 |
| EP | 1 418 172 A3 | 5/2004 |
| GB | 887413 | 1/1962 |
| GB | 1047920 | 11/1966 |
| JP | 57-116038 | 7/1982 |
| WO | WO 2004/056753 A1 | 7/2004 |
| WO | WO 2008/107226 A1 | 9/2008 |
| WO | WO 2009/144148 A1 | 12/2009 |
| WO | WO 2012/076315 A1 | 6/2012 |
| WO | WO 2012/076317 A1 | 6/2012 |
| WO | WO 2012/171830 A1 | 12/2012 |

OTHER PUBLICATIONS

International Search Report issued Sep. 27, 2012, in PCT/EP12/060577 filed Jun. 5, 2012.

\* cited by examiner

*Primary Examiner* — Sudhakar Katakam
(74) *Attorney, Agent, or Firm* — Oblon, McClelland, Maier & Neustadt, L.L.P.

(57) ABSTRACT

The present invention refers to the preparation of 3-cyano-3,5,5-trimethylcyclohexanone (isophorone nitrile, abbreviation IPN) using a calcium alkoxide, particularly calcium ethoxide, as catalyst.

21 Claims, No Drawings

PROCESS FOR PREPARING 3-CYANO-3,5,5-TRIMETHYLCYCLOHEXANONE

The present invention relates to the preparation of 3-cyano-3,5,5-trimethylcyclohexanone (isophorone nitrile, abbreviation IPN) using a calcium alkoxide, particularly calcium ethoxide, as catalyst.

The base-catalysed reaction of hydrocyanic acid (HCN) with alpha, beta-unsaturated cyclic (or acyclic) ketones is a known reaction (Hydrocyanation of Conjugated Carbonyl Compounds, Wataru Nagata and Mitsuru Yoshioka, published online: 15 Jul. 2005 DOI: 10.1002/0471264180.or025.03)

The preparation of isophorone nitrile (IPN) as precursor for the synthesis of isophorone diamine is carried out industrially.

The reaction of isophorone (IP) with HCN to give IPN can be described with the following reaction equation:

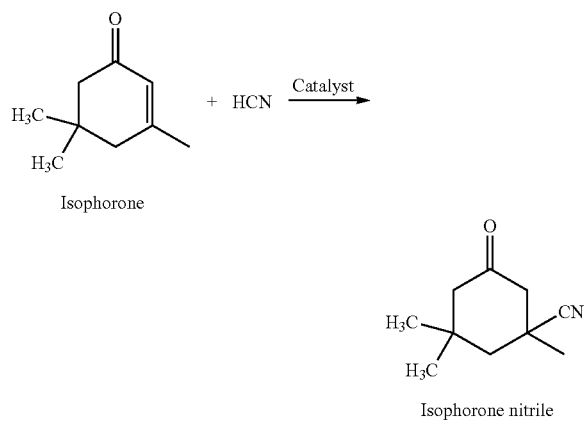

Catalysts for the preparation of beta-cyanoketones such as IPN are generally bases which provide free cyanide ions ($CN^\ominus$) for the 1,4-addition reaction. Here, a distinction is usually made between inorganic salts and organic compounds.

Hydrocyanic acid is a weak acid with a $pk_a$ of 9.21 and therefore does not by itself add to an activated carbon-carbon double bond. On the other hand, $CN^\ominus$ (like $SH^\ominus$ or $I^\ominus$) is sufficiently nucleophilic to add to an electrophilic carbon atom of a conjugated carbonyl system. Therefore, a basic catalyst is required to increase the concentration of $CN^\ominus$ ions. Possible catalysts are therefore cyanide-containing salts (for example NaCN, KCN or $K_4Ni(CN_4)$, see U.S. Pat. No. 2,904,581), inorganic bases (for example potassium carbonate or sodium hydroxide) or organic bases (for example triethylamine, pyridine or piperidine).

The rate of the addition reaction is proportional to the concentration of $CN^\ominus$ ions and the addition is reversible with respect to $CN^\ominus$. Moreover, the reaction to give the cyanohydrin competes with the reaction to give the cyanoketone (1,2-addition versus 1,4-addition). For many substrates the 1,2-addition is faster than the 1,4-addition.

The reverse reaction from the cyanoketone (for example IPN) to the corresponding starting material (for example isophorone) proceeds more slowly than the forward reaction. The reverse reaction of the reversible addition reaction is favoured with increasing temperature. Synthesis is therefore recommended at the lowest possible temperatures.

The cyanohydrin is unstable in basic media and therefore a cyanoketone is formed almost exclusively. The formation of the cyanohydrin is negligibly low (or reversible such that $CN^\ominus$ ions can react by 1,4-addition).

At an excessively high $CN^\ominus$ concentration, a spontaneous strongly exothermic dimerization and/or polymerization of the hydrocyanic acid can occur. Polymeric hydrogen cyanide, also referred to as azulmic acid, is formed by anionic polymerization of HCN. The reaction proceeds via dimeric hydrocyanic acid (iminoacetonitrile). A ring closure takes place simultaneously between two gamma-nitrile groups, whereby the catenated polymer is stabilized. It is essential to avoid this polymerization in every case, since the selectivity of the isophorone nitrile formation is adversely affected thereby.

The reaction with HCN may be carried out in solution or solvent-free.

PRIOR ART a) Method for Preparing Isophorone Nitrile from Isophorone and Hydrocyanic Acid JP06065183 The alkaline reaction mixture is mixed with an inert solvent and is processed in a thin film evaporator. The catalyst, the high-boilers and the solvent are removed. The IPN is then purified in a further column.

EP 0 554 786 (analogous to U.S. Pat. No. 5,254,711) describes a method for the continuous preparation of IPN by base-catalysed reaction of IP with HCN in two separate reaction zones. The preparation of IPN is carried out by reacting IP with hydrocyanic acid over an alkaline catalyst which forms cyanide ions. Suitable catalysts are alkali metal and alkaline earth metal alkoxides; also hydroxides and cyanides; and also quaternary ammonium bases.

DE 102 59 708 (analogous to EP 1 581 481) claims a method for preparing IPN by reaction of IP with HCN in the presence of basic catalysts—particularly calcium oxide—and addition of sulphonic acids or carboxylic acids prior to further distillative workup. By using carboxylic acids or sulphonic acids, the formation of a precipitate does not occur and the crude product can be immediately further processed.

Established catalysts and their use in process technology in the prior art affords conversions and selectivities (98% based on the conversion to IPN) usually at temperatures of >170° C. at standard pressure.

The dimerization of isophorone to diisophorone and/or polymerizations occur as possible side reactions under basic reaction conditions. The self-condensation of isophorone is described in detail in the (patent) literature:

1) J. A. Bertrand, D. Cheung, A. D. Hammerich, H. O. House, W. T. Reichle, D. Vanderveer, E. J. Zaiko, J. Org. Chem., 1977, 42, 9, 1600-1607.
2) G. Kabas, H. C. Rutz, The Alkali-Catalyzed Self-Condensation of Isophorone, Tetrahedron. 1966, 22, 1219-1226.
3) U.S. Pat. No. 2,406,652, Ketols from Isophorones and Homologues Thereof.

It is essential to inhibit this dimerization in the preparation of isophorone nitrile since this reaction is not reversible under the existing synthesis conditions and, therefore, isophorone is lost. High-boilers are usually formed which must be removed in the work-up process and the selectivity (S) is, therefore, adversely affected.

b) Catalysts for Preparing IPN from Isophorone and Hydrocyanic Acid Consisting of Basic Alkali Metal or Alkaline Earth Metal Compounds DE 10 85 871, having the title "Method for preparing alicyclic cyanoketones" (analogous to GB 887 413 Carbocyclic cyanoketones from ROHM & HAAS COMPANY), describes the preparation of cyanoketones by reacting unsaturated ketones with hydrocyanic acid over an alkaline catalyst which forms cyanide ions. Suitable catalysts are alkali metals and carbonates thereof; also alkaline earth metals and alkali metal and alkaline earth metal alkoxides, oxides, hydroxides, peroxides and cyanides; tertiary amines and quaternary ammonium bases. The catalyst is required in an amount of 0.1 to 20% by weight, based on the total weight of the reaction partners. The reaction is conducted preferably at temperatures of 150 to 225° C. and at standard pressure. The preparation of isophorone nitrile is mentioned as an example.

DE 12 40 521 Method for preparing gamma-ketocarbonitriles from alpha,beta-unsaturated ketones: the preparation of IPN is described, in which high hydrocyanic acid concentrations and heterogeneous catalysts (alkaline catalysts supported on, for example, clay fragments) are used without solvent. All substances which form cyanide ions in the presence of hydrogen cyanide under the reaction conditions are suitable as basic catalysts. These include e.g. oxides, hydroxides, cyanides and alkoxides of alkali metals and alkaline earth metals. It is essential that the catalysts have solid supports. Synthesis is effected at temperatures between 50 and 350° C. The yield of isophorone nitrile is 95.3% based on the hydrocyanic acid used, and 96.0% based on the conversion of isophorone.

DE 12 40 854 Method for preparing 3-cyano-3,5,5-trimethylcyclohexanone from isophorone and hydrocyanic acid: here a method is claimed for preparing IPN from IP and HCN in the presence of alkaline catalysts at 80-250° C. using 0.001 to 0.1% by weight of catalyst and without using solvent. Particularly suitable catalysts are alkali metal cyanides, hydroxides and alkoxides. As an example, yields of 96.2% of IPN are achieved based on the conversion of isophorone, and 97.9% of IPN based on the hydrocyanic acid used.

EP 0 433 615 includes the achievement of relatively high space time yields, a simple procedure and the avoidance of expensive catalysts and auxiliaries by using lithium hydroxide (LiOH) as catalyst. Yields of up to 96.1% of IPN are achieved, based on the hydrogen cyanide used.

EP 0 558 332 claims the use of lithium cyanide as catalyst, which was prepared beforehand from LiOH. The concentration of HCN is selected such that no free LiOH is formed. The amount of byproducts is significant.

EP 1 418 172 claims the use of a calcium oxide having a surface area of >1.5 m²/g. The reaction takes place preferably at temperatures between 150-170° C.

c) Catalysts for Preparing Isophorone Nitrile from Isophorone and Hydrocyanic Acid Consisting of Onium Compounds or the Specific Use Thereof JP 61033157 claims the preparation of IPN by reaction of hydrocyanic acid and isophorone in the presence of quaternary ammonium or phosphonium hydroxides as catalysts.

EP 0 558 799 claims the use of an onium cyanide (for example tetraalkylammonium cyanide or tributylsulfonium cyanide) as catalyst in the reaction of isophorone with HCN for preparing IPN. The reaction is carried out between 110 and 140° C. but yields up to 2% of diisophorone as a secondary component.

EP 0 671 384 (analogous to U.S. Pat. No. 5,516,928) claims the use of quaternary ammonium salts with hydrogen carbonate or alkyl carbonate counter ions. Reaction of HCN with isophorone is carried out in a temperature range between 100 and 170° C.

U.S. Pat. No. 5,183,915 describes the preparation of 3-cyano-3,3,5-trialkylcyclohexanones by reacting the respective ene-one with HCN in the absence of water. Quaternary ammonium or phosphonium cyanides are used as catalyst. A significant proportion of byproducts are formed (2.4% diisophorone).

EP 0 502 707 claims the use of quaternary ammonium or phosphonium salts and a basic cocatalyst (potassium or sodium carbonate) for the synthesis of IPN. Reaction of HCN with isophorone is carried out in a temperature range between 90 and 140° C.

Document U.S. Pat. No. 5,011,968 describes the preparation of IPN by reaction of isophorone with HCN and tetramethylammonium hydroxide as catalyst and subsequent thermal decomposition of the catalyst to trimethylamine and removal with the offgas.

d) Catalysts for Preparing Isophorone Nitrile from Isophorone and Hydrocyanic Acid by Means of Phase Transfer Catalysis or by Using a Biphasic Reaction System JP 62164656 describes the release of IPN from the corresponding acetal of IPN by acid.

EP 0 028 179 describes the preparation of IPN from isophorone (organic phase) and cyanides (aqueous phase) in a biphasic system with a phase transfer medium used in catalytic amounts. The phase transfer catalysts used are quaternary ammonium and phosphonium salts (for example tetraethylammonium bromide or disodium phosphate), which are soluble in the organic phase. The reaction time is, for example, 4 to 5 hours at 80° C.

U.S. Pat. No. 4,299,775 Method for preparing 3-cyano-3,5,5-trimethylcyclohexanone claims, as catalyst, sodium or potassium cyanide in the presence of water and an inert solvent and also an onium phase transfer catalyst.

EP 0 425 806 (DE 690 09 394T2) describes the reaction of isophorone with alkaline cyanides in stoichiometric amounts in homogeneous solution with an aqueous and organic solvent mixture, which is simultaneously and gradually neutralized with inorganic acids. The phases separate again during the reaction and may be separated from one another in this manner.

JP 04279558 claims the preparation of IPN by reacting IP with HCN in the presence of a basic catalyst and suitable amounts of water (0.1-5%) at 110-250° C. Particularly suitable catalysts are alkali metal cyanides, hydroxides and alkoxides.

e) Catalysts for Preparing Isophorone Nitrile from Isophorone and Hydrocyanic Acid by Means of Particular Organic Bases EP 0 985 659 (analogous to DE 198 36 474) shows the use of 1,3-dimethylimidazolium-4-carboxylate as catalyst at temperatures of 80 to 220° C., particularly preferably 100-180° C., and atmospheric pressure.

JP 61033158 describes the preparation of IPN by reaction of hydrocyanic acid and isophorone in the presence of diazobicycloalkenes as catalysts.

In JP 04253948, isophorone is converted to IPN with HCN in the presence of guanidine (0.01-0.5 mol based on 1 mol of isophorone) as base.

f) Catalysts for Preparing Isophorone Nitrile from Isophorone and Hydrocyanic Acid by Means of Use of Particular Solvents In JP 57116038, isophorone is converted to IPN with HCN in the presence of a basic catalyst and a glycol (for example ethylene glycol).

JP0 4164057 describes the preparation of IPN by equimolar reaction of IP with HCN under base catalysis in 1,3-dimethyl-2-imidazolidinone as solvent.

JP 04112862 includes the preparation of IPN by reaction of isophorone with HCN, alkaline catalysts and DMSO (dimethyl sulfoxide) and/or DMF (dimethylformamide) as solvents.

There exists a need for basic catalysts for the preparation of beta-cyanoketones—IPN—which are inexpensive, enable high conversion and selectivity and are active under mild reaction conditions. Moreover, the avoidance of waste products is desirable.

The object of the present invention consists, therefore, in providing a method and a catalyst for the conversion of isophorone to IPN with hydrocyanic acid at a relatively low process temperature. It was particularly important in this context to find a catalyst which fulfils the precondition to be usable in an industrial plant, particularly with high selectivity and high conversion.

Surprisingly, it has been found that calcium alkoxides, particularly calcium ethoxide, as heterogeneous catalyst in the reaction of isophorone with HCN to give isophorone nitrile (IPN), achieve the set objective.

The invention relates to a method for preparing isophorone nitrile from isophorone and hydrocyanic acid, wherein the reaction is carried out in a heterogeneous phase in the presence of a calcium alkoxide as catalyst.

Preference is given to using calcium ethoxide as catalyst.

It has been found that the catalyst, particularly the calcium ethoxide preferably used as catalyst, has the following advantages and thereby further advantages for the method have been found:

Calcium ethoxide is an inexpensive heterogeneous catalyst which may be used at process temperatures less than 170° C. with high space time yields. With such a catalyst, selectivities with respect to the desired isophorone nitrile (IPN) product of up to greater than 98% can already be achieved under standard pressure at a reaction temperature of 90° C. and the formation of byproducts (diisophorone, polymeric hydrocyanic acid and high boilers) is therefore very low. The conversion based on HCN is also up to greater than 98%. The catalyst according to the invention can be used both in a fixed-bed method and in a slurry method.

In addition, the use of the catalysts according to the invention provides a high potential for process optimization of industrial methods with regard to energy (reduction of energy requirement) at a low process temperature.

The calcium alkoxide used as catalyst, preferably the calcium ethoxide, has the following properties:

The BET surface area of the calcium alkoxide used according to the invention, preferably calcium ethoxide, is at least 5 $m^2/g$, preferably greater than 8 $m^2/g$, particularly preferably greater than 12 $m^2/g$. The measurement of the BET surface area should be carried out by the statistical volumetric multipoint method according to DIN ISO 9277 ($p/p_O$ range: 0.05-0.2) using a pulverulent sample.

A calcium alkoxide is preferably used, particularly preferably a calcium ethoxide, having an apparent density of at least 250 g/l. Apparent density is understood to mean the ratio of mass to volume [unit: g/l] of a loose, non-compacted bed. The calcium alkoxide according to the invention, preferably calcium ethoxide, is particularly preferably characterized by an apparent density in the range of 290 g/l to 550 g/l.

Particular preference is given to using calcium ethoxide. The BET surface area, measured using a pulverulent sample, of the calcium ethoxide used according to the invention is at least 5 $m^2/g$, preferably greater than 8 $m^2/g$, particularly preferably greater than 12 $m^2/g$. In addition, the calcium ethoxide has an apparent density of at least 250 g/l, preferably in the range of 290 g/l to 550 g/l. Moreover, the calcium ethoxide has an average particle size (d50 value) between 10-200 μm. These ranges mentioned here may be combined as desired.

The dynamic differential calorimetry (differential scanning calorimetry, DSC, according to DIN EN ISO 11357-1 and DIN 53765) of the calcium ethoxide preferred according to the invention gave endothermic peak(s) in the range of 70-130° C., and DSC heat flows of 0.35 to 0.55 mW/mg.

The DSC analysis should be carried out in the temperature range of –50 to 300° C. and 10 K/min in a nitrogen stream of 50-70 ml and an initial weight of 10-20 mg in an aluminium sample pan in "pierced lid mode" e.g. using a DSC NETZSCH DSC 204 F1 device.

The particle size distribution and further physical data of the calcium ethoxide used according to the invention are presented in Table 1 below. The median value of the particle size distribution, also known as the d50 value, is the most important parameter as a measure for the average particle size. 50 volume percent of the sample are finer and the other 50% are coarser than the d50 value. The d10 value is defined analogously.

TABLE 1

Physical data of the calcium alkoxide used according to the invention

| Catalyst | Appararent density of the powder [g/litre] | Particle size d10 [μm] | Particle size d50 [μm] | BET surface area [$m^2/g$] | DSC endothermic peak [° C.] | DSC heat flow [mW/mg] |
|---|---|---|---|---|---|---|
| 1 | 466 | 7 | 134 | 13 | 100 | 0.38 |
| 2 | 483 | 4 | 21 | 8 | 93 | 0.42 |
| 3 | 296 | 5 | 43 | 15 | 93 | 0.45 |
| 4 | 462 | 10 | 70 | 15 | 98 | 0.39 |

The catalyst may be present as powder, pellets, granulate, or extrudate.

The preparation of isophorone nitrile may generally be carried out under homogeneous or heterogeneous base catalysis. In the case of homogeneous catalysis, the catalyst and reactants are present in the same phase. Typically, a metal salt is dissolved in a solvent (e.g. sodium methoxide dissolved in methanol), with which the reactants react.

The advantages of the method according to the invention in a heterogeneous phase are described below. In heterogeneous catalysis used according to the invention, catalyst and reactants are present in different phases. The solid catalyst is exposed to the reactants present in the liquid phase, i.e. a phase boundary is present between the catalyst and the reaction mixture. The catalyst is a porous solid, while the reactants are gaseous and/or liquid. In the case of heterogeneously catalysed processes, the critical processes take place on the surface of the solid.

The heterogeneous catalysis used according to the invention, in contrast to the classical homogeneous catalysis, brings with it the invaluable advantage for the industrial conversion of a simple catalyst removal due to the existence of a second phase. The heterogeneous catalysis is thus a surface-controlled process, which means that physical substance transport processes, such as substance transport in porous catalysts, can significantly influence the achievable conversions and selectivities.

The resistance of a catalyst to chemical, thermal or mechanical effects determines their life time in reactors (service life of the catalyst in a fixed-bed reactor). The stability thereof can be strongly influenced by decomposition, carbonization and poisoning of the catalyst. Whether a catalyst is therefore suitable for an industrial process depends in its activity, selectivity and stability.

In the form of the calcium alkoxide, preferably calcium ethoxide, used according to the invention, catalysts have been found, surprisingly, which fulfil these requirements.

With the catalyst used according to the invention, particularly short residence times of the reaction mixture in the reactor are achievable with good yields, selectivities and high space time yields. Depending on the reaction conditions selected, the residence times are a few minutes to a few hours.

The reaction may be carried out in the presence or absence of inert solvents. Particular preference is given to using isophorone in molar excess, based on HCN, and without addition of external solvent.

Due to the low HCN concentrations necessary, charging with HCN with subsequent addition of isophorone is not advisable. At least a portion of the isophorone is therefore always present and the HCN is added at a temperature at which the addition to isophorone occurs at the desired rate. The catalyst must also be present. HCN also must not be added too slowly, since, in this case, particularly at high reaction temperatures, isophorone nitrile decomposes with reformation of HCN and isophorone.

Since—as already mentioned—the HCN must not be added such that a sufficient quantity thereof (which does not convert to cyanide ions and therefore does not add directly to the isophorone) is present in the reaction mixture for polymerization, the rate of addition of HCN to isophorone also must not be selected to be excessively high.

The method according to the invention is generally carried out such that an excess of isophorone is used, such that a relatively high selectivity for isophorone nitrile is achieved.

The molar ratio of isophorone/HCN is generally >1:1, generally 19:1 to 1.2:1, preferably 3:1 to 1.5:1.

The whole amount of isophorone may be charged and be brought to the desired reaction temperature before the HCN is added in the presence of the catalyst. It has been proven favourable to charge a portion of the isophorone and, after heating to reaction temperature, to add a mixture of isophorone and HCN in a suitable ratio in presence of the catalyst.

The catalyst may already be present during the heating of the isophorone. In contrast to the conventional catalysts used according to the prior art, particularly alkali metal salts, only minor, if any, polymerization of the isophorone occurs.

As part of the reaction parameters presented above, the HCN or the isophorone/HCN mixture is added such that a sufficiently low steady-state concentration of HCN results and a high selectivity and also a high conversion to isophorone nitrile are achieved. Only a low polymerization of HCN must occur, since the conversion and selectivity would be adversely affected thereby. The selectivity with respect to IPN should be >95%, preferably >98%, particularly preferably >99%.

The steady-state concentrations of unreacted, free HCN and the total concentration of cyanide ions (sum of free HCN and cyanide bound as the cyanohydrin of isophorone and isophorone nitrile) are preferably determined and the reaction conditions adjusted until the values are in the desired range. The determination of the cyanide ion concentrations mentioned is preferably carried out by titration.

The workup of the reaction mixture after reaction completion is conducted in a conventional manner known to those skilled in the art. Excess isophorone is preferably removed by distillation and is advantageously reused. Subsequently, the isophorone nitrile formed is separated, preferably also by distillation, from high boilers and the catalyst used.

With the basic catalysts used according to the prior art, a partial polymerization of the HCN and side reactions of the isophorone (dimerization and polymerizations) occur. It is preferable to suppress this reaction by a low free concentration of cyanide ions. This implies a high conversion of HCN. In the method according to the invention, a conversion of at least 70% is achieved. Depending on the catalyst concentration selected, conversions of >95%, preferably >98%, particularly preferably >99%, can be achieved, even at a reaction temperature of 90° C.

A further advantage of the method according to the invention is its ecological and economic performance. The catalytic reaction is preferably carried out at a reaction temperature in the range of 80 to 180° C., particularly preferably 80 to 130° C. and especially preferably 80 to 100° C.

The reaction is carried out at pressures of 0.01 to 10 bar, preferably 1 to 5 bar, particularly preferably at standard pressure (atmospheric pressure).

The method according to the invention therefore has the advantage that it may be carried out inexpensively and profitably and also, owing to the short reaction time, affords a relatively large conversion per unit time.

The reaction time required for the catalytic reaction is preferably 5 minutes to 180 minutes, particularly preferably 5 minutes to 90 minutes.

These reaction times are considerably shorter in comparison to the prior art. The examples from the documents mentioned above show that both the reaction times and the reaction temperatures are considerably longer and higher respectively than in the method according to the invention and a distinctly increased energy expenditure is therefore required to carry out the reaction.

The method according to the invention may be carried out continuously, in batch mode or semi-continuously.

In a preferred embodiment, the reaction procedure is carried out in a stirred tank, a stirred tank cascade, a flow tube, one or more fixed-bed reactors or a column. The catalytic reaction is carried out over a heterogeneous catalyst.

According to the arrangement of the solid phase in the reaction apparatus, two classes of reactors for heterogeneously catalysed reaction processes are in principle distinguished and may be used in the method according to the invention:

1. The solid phase is arranged immobilized in the reactor (fixed-bed method, e.g. fixed-bed reactor), 2. The catalyst is mobile (slurry method, e.g. suspension reactor).

The method according to the invention may be carried out by means of a triphasic reaction. In triphasic reactions, i.e. in gas-liquid-solid processes, the solid acts as catalyst. The reactants may be present both in the gas phase and in the liquid phase. The fluid phases may also partially contain reaction product.

The heterogeneously catalysed reaction in (semi)-batchwise suspension reactors according to 2. may be carried out in the scope of the invention.

A fixed-bed reactor according to 1. is particularly preferably used according to the invention.

According to the invention, the method is preferably carried out in a continuously operated fixed-bed reactor. In this case, a filtration of the catalyst according to method variant 2. is obviated and very high space time yields can be achieved.

The method according to the invention is especially preferably carried out biphasically, preferably by means of a continuously operated fixed-bed reactor with presaturator. In the latter, the liquid is saturated with gas (also HCN) and then only the saturated liquid is piped into a fixed-bed reactor. Thus, a biphasic system results (liquid/solid). In this case, isophorone is particularly preferably used in molar excess, based on HCN, and isophorone is, therefore, the solvent and no external solvent is used.

The invention also relates to the use of calcium alkoxide, preferably calcium ethoxide, as catalyst for preparing isophorone nitrile from isophorone and hydrocyanic acid, wherein the reaction is carried out in a heterogeneous phase, preferably biphasic, preferably in a fixed-bed reactor. Alternatively, the reaction may be carried out in a suspension reactor. Preference is given to using particulate calcium ethoxide having a BET surface area of the calcium ethoxide, measured using a pulverulent sample, of at least 5 $m^2/g$, preferably greater than 8 $m^2/g$, particularly preferably greater than 12 $m^2/g$, and wherein the calcium ethoxide has an apparent density of at least 250 g/l, preferably in the range of 290 g/l to 550 g/l, wherein the ranges may be combined as desired.

EXAMPLES AND COMPARATIVE EXAMPLES

The experiments for the formation of isophorone nitrile from isophorone and hydrocyanic acid by means of various homogeneous and heterogeneous catalysts were carried out isothermally and batchwise or semi-continuously in a stirred tank apparatus equipped with dropping funnel and reflux condenser. The procedure was carried out such that the main amount of isophorone (711 g) and a portion of the hydrocyanic acid (7 g (stabilized with 0.5-1.0% phosphoric acid)) were charged in the reactor and were brought to the desired reaction temperature. The remaining hydrocyanic acid (61 g) was added as a mixture with isophorone (118 g) via a dropping funnel. The t=0 time point was defined as the addition of the catalyst. Shortly before the addition of the catalyst, the composition of the reaction mixture was determined by means of a sample and gas chromatographic analysis, to allow for possible changes during the heating phase. After addition of the catalyst, the remaining amount of hydrocyanic acid/isophorone was added continuously in a dropwise manner. The addition of the hydrocyanic acid must not be carried out too rapidly since otherwise it leads to a polymerization of the hydrocyanic acid by the cyanide ions formed. In this case, a brown polymeric solid is formed which must be removed. Samples were taken and analysed (determination of the cyanide content by titration and GC determination) at various time points. After the reaction was complete, stirring was continued for 30 minutes.

Gas Chromatographic Determination of the Reaction Products:
  Instrument: HP3/Agilent GC 6890
  Separation column: HP-5 Agilent (19091J-433) 30 m×250 µm×0.25 µm nominal
  Const. Flow: 0.9 ml/min
  Injector: Temperature: 200° C.
  Total Flow: 84.6 ml/min
  Split Flow: 81.1 ml/min (1:94.8)
  Detector: Temperature: 250° C.
  $H_2$ Flow: 40 ml/min
  Air Flow: 450 ml/min
  Make-up Flow ($N_2$): 45 ml/min
  Oven: Temperature program: 90° C./3 min at 5° C./min to 150° C. at 10° C./min to 300° C./29 min
  Sample preparation: 1000 mg sample+70 mg C-12 as ISTD in 10 ml of toluene
  Injection volume: 1.0 µl
  Evaluation: ISTD %

TABLE 2

Comparative examples using homogeneous catalysts

| | Compound class | | | | |
|---|---|---|---|---|---|
| | Alkoxide | Alkoxide | Alkoxide | Alkoxide | Alkoxide |
| Homogeneous catalyst | LiOMe | KOMe | NaOMe | NaOMe | NaOMe |
| Amount of catalyst [g] | 6.0 | 4.4 | 3.4 | 3.4 | 3.4 |
| Temperature [° C.] | 150 | 150 | 150 | 120 | 90 |
| HCN conversion [%] | 98 | 93 | 98 | 82 | 54 |
| Yield (IPN in %) | 45 | 40 | 46 | 32 | 20 |
| Selectivity (IPN in %) | 95 | 98 | 99 | 99 | 98 |
| Reaction time [min] | 345 | 266 | 305 | 215 | 216 |

Conclusion: various alkoxides as homogeneous catalysts show a good performance at 150° C. with respect to yield and selectivity; in particular, NaOMe as homogeneous catalyst shows a very good performance. However, the conversion decreases significantly with decreasing temperature.

TABLE 3

Comparative examples using heterogeneous catalysts

| Compound class | Oxide | Oxide | Carbonate | Carbonate | Carbonate | Carbonate |
|---|---|---|---|---|---|---|
| Heterogeneous catalyst | MgO (>98%) | CaO (>95%) | $Li_2CO_3$ (>99%) | $Na_2CO_3$ (>99%) | $K_2CO_3$ (>99%) | $CaCO_3$ (>99%) |
| Manufacturer/supplier | Fluka | Fels-Werke | Aldrich | Riedel de Haen | Merck | Aldrich |
| Amount of catalyst [g] | 10.0 | 10.0 | 10.0 | 10.0 | 10.0 | 10.0 |
| Temperature [° C.] | 170 | 170 | 170 | 170 | 170 | 170 |
| HCN conversion [%] | 24 | 96 | 17 | 82 | 95 | <1 |
| Yield (IPN in %) | 1 | 43 | 0.6 | 42 | 42 | <1 |
| Selectivity (IPN in %) | 67 | 99 | 67 | 92 | 99 | 6 |
| Reaction time [min] | 248 | 145 | 103 | 202 | 120 | 102 |

Conclusion: multifarious basic heterogeneous catalysts show a partially acceptable performance with respect to yield and selectivity at high temperatures of T=170° C. However, the reaction times and the reaction temperatures are relatively high.

TABLE 4

Examples according to the invention
The particulate Ca(OEt)₂ catalyst used has the following properties:
BET: 17 m²/g
Particle size: 20 μm (d50 value)
Apparent density: 460 g/L

| Compound class | Alkoxide | Alkoxide | Alkoxide | Alkoxide | Alkoxide | Alkoxide |
|---|---|---|---|---|---|---|
| Heterogeneous catalyst | Ca(OEt)₂ | Ca(OEt)₂ | Ca(OEt)₂ | Ca(OEt)₂ | Ca(OEt)₂ | Ca(OEt)₂ |
| Amount of catalyst [g] | 2.05 | 2.05 | 2.05 | 2.05 | 4.10 | 8.20 |
| Temperature [° C.] | 150 | 130 | 110 | 90 | 90 | 90 |
| HCN conversion [%] | 97 | 92 | 83 | 75 | 96 | >99 |
| Yield (IPN in %) | 44 | 41 | 37 | 33 | 44 | 45 |
| S (IPN based on IP) | >99 | >99 | >99 | >99 | 99 | 95 |
| Reaction time [min] | 76 | 76 | 76 | 76 | 71 | 76 |

Conclusion: An outstanding performance with respect to conversion, selectivity and low reaction time is established with the heterogeneous catalyst Ca(OEt)₂ according to the invention. Even at 90° C., the Ca(OEt)₂ according to the invention shows an excellent yield of IPN at virtually constant high selectivity. Depending on the amount of catalyst used, an HCN conversion of up to greater than 99% is achieved.

The invention claimed is:

1. A method for preparing isophorone nitrile, the method comprising:
   reacting isophorone and hydrocyanic acid to form isophorone nitrile in a heterogeneous phase in the presence of a calcium alkoxide catalyst at a reaction temperature of from 80 to 130° C. for a reaction time of from 5 to 180 minutes,
   wherein a BET surface area of the calcium alkoxide is at least 5 m²/g.

2. The method of claim 1, wherein the calcium alkoxide has an apparent density of at least 250 g/l.

3. The method of claim 1, wherein the calcium alkoxide catalyst is calcium ethoxide.

4. The method of claim 3, wherein
   the calcium ethoxide has a BET surface area, measured with a pulverulent sample, of at least 5 m²/g, and an apparent density of at least 250 g/l.

5. The method of claim 3, wherein the calcium ethoxide has at least one endothermic peak in the range of 70-130° C. and DSC heat flows of from 0.35 to 0.55 mW/mg in DSC.

6. The method of claim 3, wherein the calcium ethoxide has an average particle size represented by a d50 value of from 10 to 200 μm.

7. The method of claim 3, wherein the calcium ethoxide has a BET surface area of greater than 8 m²/g, and an apparent density in the range of 290 g/l to 550 g/l.

8. The method of claim 3, wherein the calcium ethoxide has a BET surface area of greater than 12 m²/g, and an apparent density in the range of 290 g/l to 550 g/l.

9. The method of claim 1, wherein the catalyst is present as powder, pellets, granulate, or extrudate.

10. The method of claim 1, wherein said reacting occurs in the presence or absence of at least one inert solvent.

11. The method of claim 1, wherein isophorone is present in a molar excess, based on hydrocyanic acid, and no external solvent is added.

12. The method of claim 1, wherein a molar ratio of isophorone/hydrocyanic acid is >1:1.

13. The method of claim 1, wherein a molar ratio of isophorone/hydrocyanic acid is from 19:1 to 1.2:1.

14. The method of claim 1, wherein a portion of isophorone is charged and, after heating to a reaction temperature, a mixture of isophorone and hydrocyanic acid is added in a molar ratio of isophorone/hydrocyanic acid >1:1 in the presence of the catalyst.

15. The method of claim 1, wherein said reacting occurs at the reaction temperature of from 80 to 100° C.

16. The method of claim 1, wherein said reacting occurs at from 0.01 to 10 bar.

17. The method of claim 1, wherein the reaction time is from 5 minutes to 90 minutes.

18. The method of claim 1, wherein said reacting is carried out biphasically.

19. The method of claim 1, wherein said reacting is carried out in a fixed-bed reactor operated in a continuous mode.

20. The method of claim 1, wherein said reacting is carried out biphasically with a fixed-bed reactor operated in a continuous mode with a presaturator.

21. The method of claim 1, wherein said reacting is carried out by a slurry method.

* * * * *